US008992770B2

(12) United States Patent
Gong et al.

(10) Patent No.: US 8,992,770 B2
(45) Date of Patent: Mar. 31, 2015

(54) EVALUATION OF DISTILLATE COMPOSITION OF A CRUDE

(71) Applicant: ExxonMobil Research and Engineering Company, Annandale, NJ (US)

(72) Inventors: Liezhong Gong, Basking Ridge, NJ (US); Corry S. Powers, Centreville, VA (US); Helen S. Wellons, Annandale, NJ (US); Tahmid I. Mizan, Coppell, TX (US); Eric D. Joseck, Burke, VA (US); Steven Webster Levine, Flemington, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 257 days.

(21) Appl. No.: 13/832,534

(22) Filed: Mar. 15, 2013

(65) Prior Publication Data
US 2014/0262957 A1 Sep. 18, 2014

(51) Int. Cl.
G01N 33/26 (2006.01)
G01N 33/28 (2006.01)
G01N 33/30 (2006.01)
G01N 24/00 (2006.01)
G01N 24/08 (2006.01)
G01N 30/02 (2006.01)
G01N 30/90 (2006.01)

(52) U.S. Cl.
CPC ............ *G01N 33/30* (2013.01); *G01N 33/2823* (2013.01)
USPC .......................................................... 208/291

(58) Field of Classification Search
CPC ... G01N 33/26; G01N 33/28; G01N 33/2811; G01N 33/2835; G01N 33/2882; G01N 24/00; G01N 24/08; G01N 30/02; G01N 30/90
See application file for complete search history.

(56) References Cited

U.S. PATENT DOCUMENTS

| | | | |
|---|---|---|---|
| 6,317,654 B1 | 11/2001 | Gleeson et al. | |
| 7,642,095 B2 * | 1/2010 | Wang et al. | 436/60 |
| 2010/0174494 A1 | 7/2010 | De Peinder et al. | |

OTHER PUBLICATIONS

The International Search Report and Written Opinion of PCT/US2014/017249 dated Apr. 23, 2014.
Jacob, S.M. et al., "Compositional Modeling Reduces Crude-Analysis Time, Predicts Yields," Oil and Gas Journal, 1998, vol. 96, No. 27, pp. 51-58.
Behrenbruch et al., "Classification and characterization of crude oils based on distillation properties," Journal of Petroleum Science and Engineering, 2007, vol. 57, No. 1-2, pp. 166-180.
Pirro, D.M. et al., "Chapter 2: Refining processes and lubricant base stocks," Lubrication Fundamentals, 2001, pp. 7-36.

* cited by examiner

Primary Examiner — Brian McCaig
(74) Attorney, Agent, or Firm — Larry E. Carter; Robert A. Migliorini

(57) ABSTRACT

Methods are provided for characterizing crude oils, crude fractions, or other potential feedstocks for forming lubricating base oils in order to determine the suitability of a feedstock for lubricating base oil production. One type of characterization is to determine the isoparaffin, naphthene, and/or aromatics contents of the distillate portion of a feedstock. A second characterization is to determine the viscosity index of a distillate portion of a feedstock after dewaxing the distillate portion to a target pour point.

17 Claims, 3 Drawing Sheets

US 8,992,770 B2

EVALUATION OF DISTILLATE COMPOSITION OF A CRUDE

FIELD

Methods are provided for evaluating the ability of crude oil or crude fraction to serve as a feedstock for production of lubricant base oils.

BACKGROUND

In lubes solvent extraction and dewaxing refining processes, rapid identification of the ability for a crude oil, crude fraction, or other potential lube feedstock for making a desirable lubricating oil is important for screening and economic evaluation of potential feedstocks. Early determination of the ability for a (crude) feedstock to make a desirable lubricating oil can allow previously undemonstrated crudes to be quickly processed into lubes, leading to more lubes feedstock flexibility and better refinery profitability. In this process, quick differentiation of "challenged" crudes from normal lubes is valuable, since "challenged" lube crudes should not be processed into lubes at a high percentage within a feed slate for quality and/or economic reasons. Otherwise, off-spec dewaxed oils (DWO) from "challenged" crudes might be generated during refinery processing, which could result in downgrade of valuable DWO into an FCC feedstock.

SUMMARY

In an aspect, a method of evaluating a feedstock is provided. The method includes obtaining an isoparaffin content of a first distillate fraction from a first portion of a feedstock; determining that the isoparaffin content of the first distillate fraction is greater than a threshold level for isoparaffin content, the threshold level for isoparaffin content corresponding to an isoparaffin content of at least 12 wt %; determining that at least one of a naphthene content and an aromatics content of the first distillate fraction is within threshold levels; and solvent dewaxing at least a portion of a second distillate fraction from a second portion of the crude oil to form a lubricant base oil.

In another aspect, a method of evaluating a feedstock is provided. The method includes obtaining an isoparaffin content of a first distillate fraction from a first portion of a feedstock; determining that the isoparaffin content of the first distillate fraction is less than a threshold level for isoparaffin content, the threshold level for isoparaffin content corresponding to an isoparaffin content of at least 12 wt %; separating at least a portion of a second distillate fraction from a second portion of the crude oil to form a separated distillate fraction having a kinematic viscosity between 3.5 cSt and 16.5 cSt; solvent dewaxing at least a portion of the separated distillate fraction to a pour point target temperature to form a solvent dewaxed fraction; measuring the viscosity index of the solvent dewaxed fraction; determining that the viscosity index of the solvent dewaxed fraction is greater than a threshold viscosity index value; solvent dewaxing at least a portion of a third distillate fraction from a third portion of the crude oil to form a lubricant base oil.

DETAILED DESCRIPTION

Figures 1A, 1B:
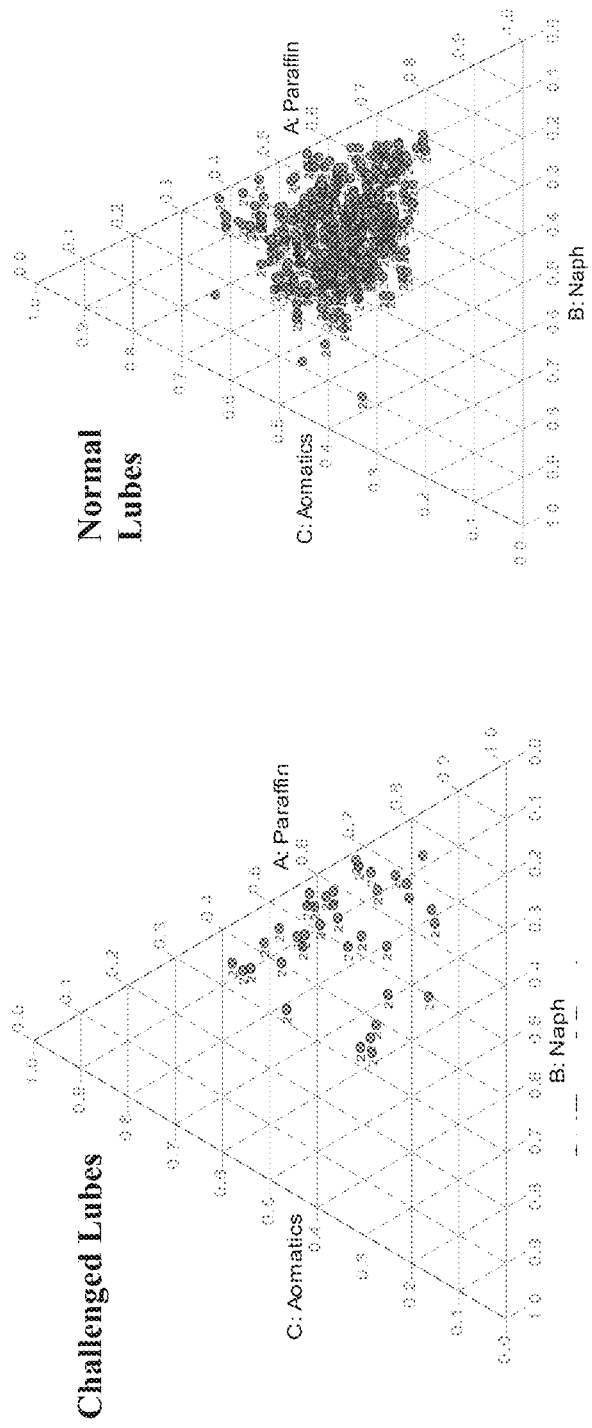
FIG. 1 shows a three-axis plot representing paraffin content, naphthene content, and aromatics content for a crude sample.

All numerical values within the detailed description and the claims herein are modified by "about" or "approximately" the indicated value, and take into account experimental error and variations that would be expected by a person having ordinary skill in the art.

Overview

In various embodiments, methods are provided for characterizing crude oils, crude fractions, or other potential feedstocks for forming lubricating base oils in order to determine the suitability of a feedstock for lubricating base oil production. One type of characterization is to determine the isoparaffin content of a waxy distillate portion of a feedstock. It has been determined that crude fractions that have low suitability for lubricant base oil production also generally have an isoparaffin content of 12 vol % or less. This is in contrast to the paraffin content of a waxy distillate fraction, which does not appear to have a strong correlation with the suitability of a feedstock for lubricant base oil production.

While determining the isoparaffin content of a waxy distillate fraction provides a way to exclude feedstocks with lower suitability, some feedstocks that are suitable for lubricating oil production are also excluded by this metric. A second method for characterizing a feedstock is to determine the viscosity index (VI) of a dewaxed distillate fraction at a defined pour point value, such as −9° C. Feedstocks that are less suitable for lubricating base oil production can have a negative VI value at a pour point of −9° C., while feedstocks that are suitable can have a positive VI value. Thus, feedstocks that have a distillate fraction with both an isoparaffin content of 12 vol % or less and a dewaxed distillate VI that is negative can be identified as feedstocks that are not suitable for lubricating base oil production. Feedstocks with distillate fraction having a low isoparaffin content (12 vol % or less) but a positive VI at −9° C. for the dewaxed distillate can be identified as suitable, and incorporated into a crude slate for production of lubricating base oils.

Group I basestocks or base oils are defined as base oils with less than 90 wt % saturated molecules and/or at least 0.03 wt % sulfur content. Group I basestocks also have a viscosity index (VI) of at least 80 but less than 120. Group II basestocks or base oils contain at least 90 wt % saturated molecules and less than 0.03 wt % sulfur. Group II basestocks also have a viscosity index of at least 80 but less than 120. Group III basestocks or base oils contain at least 90 wt % saturated molecules and less than 0.03 wt % sulfur, with a viscosity index of at least 120. In addition to the above formal definitions, some Group I basestocks may be referred to as a Group I+ basestock, which corresponds to a Group I basestock with a VI value of 103 to 108. Some Group II basestocks may be referred to as a Group II+ basestock, which corresponds to a Group II basestock with a VI of at least 113. Some Group III basestocks may be referred to as a Group III+ basestock, which corresponds to a Group III basestock with a VI value of at least 140.

Conventionally, a feedstock for lubricant base oil production is processed either using solvent dewaxing or using catalytic dewaxing. In an example of solvent dewaxing in a lube solvent plant, a vacuum gas oil (VGO) or another suitable feed is fractionated into light neutral (LN) and heavy neutral (HN) distillates and a bottom fraction by some type of vacuum distillation. The bottoms fraction is subsequently deasphalted to recover an asphalt fraction and a brightstock. The LN distillate, HN distillate, and brightstock are then solvent extracted to remove the most polar molecules as an extract and corresponding LN distillate, HN distillate, and brighstock raffinates. The raffinates are then solvent dewaxed to obtain a LN distillate. HN distillate, and brightstock basestocks with acceptable low temperature properties. It is beneficial to hydrofinish the lubricant basestocks either before or after the solvent dewaxing step. The resulting lubricant basestocks may contain a significant amount of aromatics (up to 25%) and high sulfur (>300 ppm). Thus, the typical base oils formed from solvent dewaxing alone are Group I basestocks. As an alternative, a raffinate hydroconversion step can be performed prior to the solvent dewaxing. The hydroconversion is essentially a treatment under high $H_2$ pressure in presence of a metal sulfide based hydroprocessing catalyst which remove most of the sulfur and nitrogen. The amount of conversion in the hydroconversion reaction is typically tuned to obtain a predetermined increase in viscosity index and 95%+ saturates. This allows the solvent dewaxed lubricant basestock products to be used as Group II or Group II+ basestocks. Optionally, the wax recovered from a solvent dewaxing unit may also be processed by catalytic dewaxing to produce Group III or Group III+ lubricant basestocks.

Feedstocks

A wide range of petroleum and chemical feedstocks can be processed in accordance with the disclosure. Suitable feedstocks include whole and reduced petroleum crudes, atmospheric and vacuum residua, atmospheric and vacuum gas oils, and/or other feeds that contain a distillate portion suitable for formation of lubricant base oils. A crude oil fraction is defined herein to include fractions of a whole crude that are generated by distillation of a crude. Crude fractions, unless otherwise specified, are defined herein to include crude oils that have been at least partially processed, such as synthetic crudes and/or other crude oils formed from tar sands or other non-traditional source. The method can be applied to a crude oil or crude fraction from a single source or to a mixture of crude oils and/or crude fractions.

One way of defining a feedstock is based on the boiling range of the feed. One option for defining a boiling range is to use an initial boiling point for a feed and/or a final boiling point for a feed. Another option, which in some instances may provide a more representative description of a feed, is to characterize a feed based on the amount of the feed that boils at one or more temperatures. For example, a "T5" boiling point for a feed is defined as the temperature at which 5 wt % of the feed will boil off. Similarly, a "T50" boiling point is a temperature at 50 wt % of the feed will boil. The percentage of a feed that will boil at a given temperature can be determined by the method specified in ASTM D2887.

Some suitable feeds can correspond to whole crudes. Such feeds can have a broad boiling point range that includes both fuels and lubricant boiling range portions. For more narrowly cut feeds that are still suitable for forming a lubricant oil, typical feeds can include, for example, feeds with an initial boiling point of at least 650° F. (343° C.), or at least 700° F. (371° C.), or at least 750° F. (399° C.). Alternatively, a feed may be characterized using a T5 boiling point, such as a feed with a T5 boiling point of at least 650° F. (343° C.), or at least 700° F. (371° C.), or at least 750° F. (399° C.). In some aspects, the final boiling point of the feed can be at least 1100° F. (593° C.), such as at least 1150° F. (621° C.) or at least 1200° F. (649° C.). In other aspects, a feed may be used that does not include a large portion of molecules that would traditional be considered as vacuum distillation bottoms. For example, the feed may correspond to a vacuum gas oil feed that has already been separated from a traditional vacuum bottoms portion. Such feeds include, for example, feeds with a final boiling point of 1150° F. (621° C.), or 1100° F. (593° C.) or less, or 1050° F. (566° C.) or less. Alternatively, a feed may be characterized using a T95 boiling point, such as a feed with a T95 boiling point of 1150° F. (621° C.) or less, or 1100° F. (593° C.) or less, or 1050° F. (566° C.) or less. An example of a suitable type of feedstock is a wide cut vacuum gas oil (VGO) feed, with a T5 boiling point of at least 700° F. (371° C.) and a T95 boiling point of 1100° F. or less. Optionally, the initial boiling point of such a wide cut VGO feed can be at least 700° F. and/or the final boiling point can be at least 1100° F. It is noted that feeds with still lower initial boiling points and/or T5 boiling points may also be suitable, so long as sufficient higher boiling material is available so that the feedstock is suitable for lubricant base oil production. Fractional weight boiling points, such as T5 boiling points, can be calculated by any convenient method, such as the method specified in ASTM method D2887.

If a broader boiling range feed is used, the feedstock can initially be distilled to form a distillate fraction. The cut point for separating a distillate fraction from other lower boiling portions of the feed can correspond to any of the T5 boiling points described above. The distillate fraction can also be separated from a resid or bottoms portion of the feed. The cut point for separating the distillate fraction from the vacuum resid or bottoms portion can be at least 950° F. (510° C.), such as at least 1000° F. (538° C.). Additionally or alternately, the cut point for separating the distillate fraction from the vacuum resid can be 1100° F. (593° C.) or less.

As an alternative to selecting a cut point for separating a distillate portion from a feedstock based on a temperature, another option is to select a cut point so that the resulting distillate fraction will have a desired kinematic viscosity. For example, if it is desired to form a 100N visgrade base oil from the distillate fraction, the cut point for forming the distillate fraction can be selected so that the kinematic viscosity of the distillate fraction at 100° C. is between 3.8 cSt and 4.2 cSt. If a 150N visgrade base oil is desired, the cut point for forming the distillate fraction can be selected so that the kinematic viscosity of the distillate fraction at 100° C. is between 5.1 cSt and 5.8 cSt. If a 600N visgrade base oil is desired, the cut point for forming the distillate fraction can be selected so that the kinematic viscosity of the distillate fraction at 100° C. is between 13.8 cSt and 16.2 cSt.

In some aspects, the sulfur content of the feed can be at least 300 ppm by weight of sulfur, or at least 1000 wppm, or at least 2000 wppm, or at least 4000 wppm, or at least 10,000 wppm, or at least 20,000 wppm. In other embodiments, including some embodiments where a previously hydrotreated and/or hydrocracked feed is used, the sulfur content can be 2000 wppm or less, or 1000 wppm or less, or 500 wppm or less, or 100 wppm or less.

Processing to Form Distillate and Dewaxed Distillate Fractions

In some embodiments, the feedstock for characterization can correspond to a distillate boiling range feedstock. In other embodiments, one or more separation processes can be used to separate the distillate boiling range portion of a feedstock, such as a portion boiling from at least 650° F. (343° C.) to 1100° F. (593° C.) or less, from the other portions of a feedstock. One example of a possible separation can be to use an atmospheric distillation column to separate lower boiling components of a feedstock from a bottoms portion (or optionally a bottoms portion and one or more other distillate portions). This atmospheric bottoms portion can then be passed into a vacuum distillation column to separate the lower boiling portions from a vacuum bottoms portion. Other potential configurations for separating a desired distillate boiling range portion of a whole or partial crude oil (or another wide boiling feedstock) from other portions of the feedstock can also be used.

After forming the distillate fraction from a crude oil or other feedstock, the distillate fraction can be characterized as described below to determine the isoparaffin, aromatic, and naphthene content of the distillate fraction. Optionally, the distillate fraction can then be solvent dewaxed in order to facilitate determination of the viscosity index for the dewaxed distillate fraction.

Solvent dewaxing typically involves mixing a feed with chilled dewaxing solvent to form an oil-solvent solution. Precipitated wax is thereafter separated by, for example, filtration. The temperature and solvent are selected so that the oil is dissolved by the chilled solvent while the wax is precipitated. Optionally, an aromatics extraction can be performed on the distillate prior to solvent dewaxing, so that the solvent dewaxing is performed on the raffinate from aromatics extractions.

An example of a suitable solvent dewaxing process involves the use of a cooling tower where solvent is prechilled and added incrementally at several points along the height of the cooling tower. The oil-solvent mixture is agitated during the chilling step to permit substantially instantaneous mixing of the prechilled solvent with the oil. The prechilled solvent is added incrementally along the length of the cooling tower so as to maintain an average chilling rate at or below 10° F. per minute, usually between 1 to 5° F. per minute. The final temperature of the oil-solvent/precipitated wax mixture in the cooling tower will usually be between 0 and 50° F. (−17.8 to 10° C.). The mixture may then be sent to a scraped surface chiller to separate precipitated wax from the mixture.

Representative dewaxing solvents are aliphatic ketones having 3-6 carbon atoms such as methyl ethyl ketone and methyl isobutyl ketone, low molecular weight hydrocarbons such as propane and butane, and mixtures thereof. The solvents may be mixed with other solvents such as benzene, toluene or xylene.

In general, the amount of solvent added will be sufficient to provide a liquid/solid weight ratio between the range of 5/1 and 20/1 at the dewaxing temperature and a solvent/oil volume ratio between 1.5/1 to 5/1. The solvent dewaxed oil is typically dewaxed to a desired pour point. For the dewaxed distillate viscosity index test described below, one option is to use solvent dewaxing to achieve a pour point value of −9° C. Alternatively, the solvent dewaxing can be used to achieve other convenient pour points that are useful for characterizing the distillate in order to determine a viscosity index at a given temperature, such as a viscosity index at −9° C.

Isoparaffin Evaluation Versus Paraffin Evaluation

Based on an initial feedstock, or after forming a distillate fraction from the initial feedstock, the distillate fraction can be characterized with regard to the types of compounds in the fraction. One characterization method that is sometimes used for characterization of naphtha fractions with a boiling point of 200° C. or less is to determine the percentages of three types of compounds within the naphtha fraction: paraffins, aromatics, and naphthenes. This type of information can be generated using standard laboratory techniques, such as gas chromatography and/or NMR analysis and/or other methods.

For such a naphtha fraction, ASTM D5443 specifies a test method for determining the amounts of paraffin, aromatics, and naphthene in the fraction.

For a distillate fraction suitable for lubricant base oil formation, the boiling range is significantly higher than the boiling range for the naphtha fractions specified in ASTM D5443. However, standard laboratory analysis methods can still be used to determine the paraffin, aromatics, and naphthene content of a distillate fraction. Such analysis methods include gas chromatography methods, NMR analysis, and/or other characterization methods. For example, the distillate portion of a wider boiling range feedstock can be characterized directly, without forming a separate distillate fraction, by using techniques such as high pressure liquid chromatography (HPLC) and/or gas chromatography time-of-flight mass spectrometry to characterize the compounds within the desired distillate boiling range.

FIGS. 1a and 1b show examples of a 3-axis plot showing the paraffin, aromatic, and naphthene contents for the distillate portions of a variety of crude oils. In FIG. 1b, the paraffin, aromatic, and naphthene contents are shown for a large number of crude oils that are suitable for lubricant base oil production. In other words, the crude oils represented in FIG. 1b include a distillate fraction that, when solvent dewaxed, leads to a suitable Group I base oil. FIG. 1a shows a similar 3-axis plot for a number of "challenged" crudes. The crude oils represented in FIG. 1a include a distillate fraction that, when solvent dewaxed, does not lead to a lubricant base oil that meets conventional specifications for a Group I base oil.

As shown in FIGS. 1a and 1b, the paraffin, aromatics, and naphthene 3-axis plots for challenged crudes and suitable crudes does not show any pattern or distinction that distinguishes between the two types of crudes. The range of values for the challenged crudes in FIG. 1a appears to be similar to the range of values for the suitable crudes in FIG. 1b. This shows that a characterization of the distillate portion of crude oil fractions based on paraffin, aromatics, and naphthene content provides only minimal guidance with regard to the suitability of a crude for lubricant base oil production.

Figures 2A, 2B:
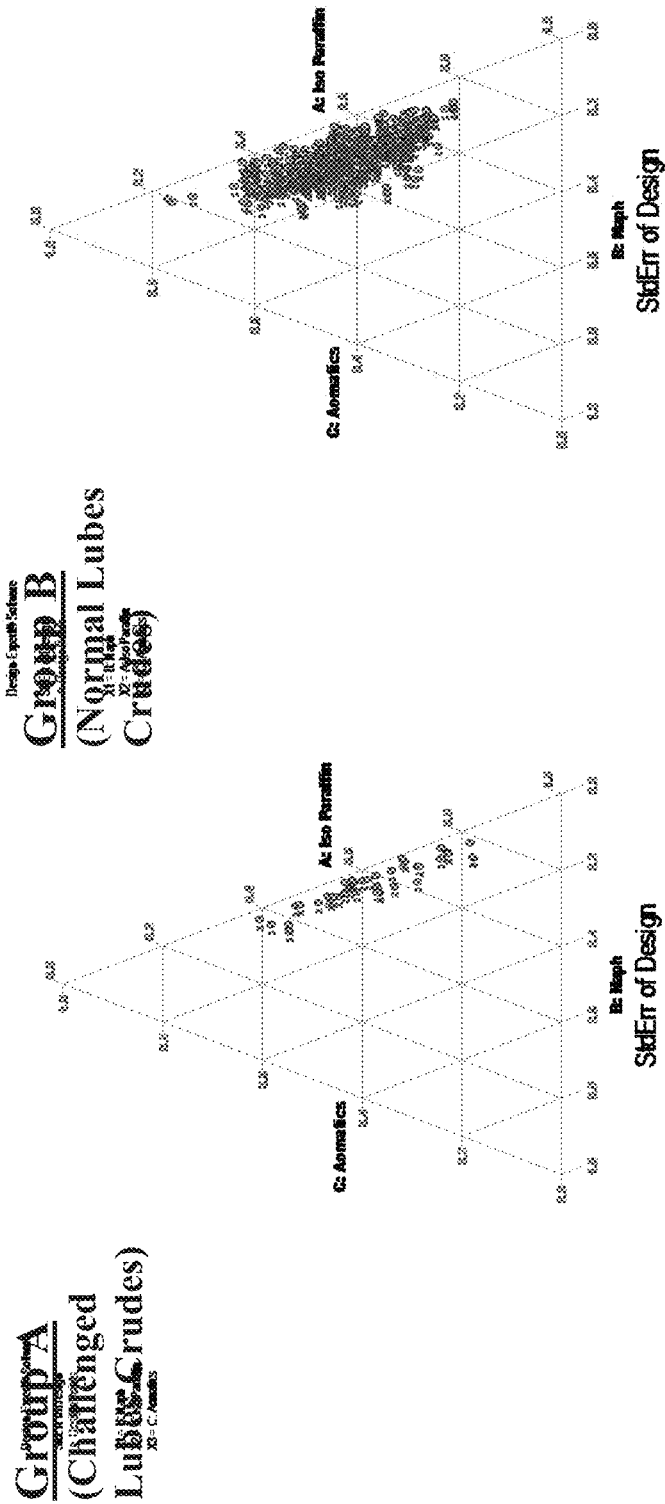
FIG. 2 shows a three-axis plot representing isoparaffin content, naphthene content, and aromatics content for a crude sample.

Based on the above, the paraffin, aromatics, and naphthene comparison traditionally used for characterizing naphtha fractions provides only minimal assistance in identifying suitable crudes for base oil production. However, an alternative type of characterization can be used to identify a broad category of crude oils (and other feedstocks) that includes challenged crudes/feedstocks within the category. FIGS. 2a and 2b also show a type of 3-axis plot for the same crude samples shown in FIGS. 1a and 1b. In FIGS. 2a and 2b, the 3-axis plot shows the isoparaffin, aromatics, and naphthene content for the distillate portions of challenged crudes and suitable crudes, respectively. In the 3-axis plots shown in FIGS. 2a and 2b, rather than characterizing the total paraffin content of the distillate portion of a crude or crude fraction, only the isoparaffin portion is characterized. This excludes the straight chain (waxy) paraffins within a distillate fraction from the characterization. As shown in FIGS. 2a and 2b, characterizing the challenged crudes based on isoparaffins instead of paraffins results in a clustering of data for the challenged crudes. In particular, the challenged crudes in FIG. 2a all show an isoparaffin content of 12 wt % or less. This is in contrast to the suitable crudes or crude fractions in FIG. 2b, which include samples with isoparaffin contents both greater than and less than 12 wt %. Thus, one option for identifying challenged crudes (and/or crude fractions and/or other feedstocks) with reduced suitability for lubricant base oil production is to simply identify crudes that have a distillate portion with an isoparaffin content of greater than 12 wt %. The value of 12 wt % corresponds to a threshold level for isoparaffin content. For such suitable feedstocks, the aromatics content of the distillate portion can be between threshold levels of 15 wt % to 80 wt %, while the naphthene content of the distillate portion can be between threshold levels of 20 wt % to 80 wt %. Other suitable threshold levels can be determined for use in evaluating a crude oil for suitability. Other suitable threshold values can be determined, for example, by using a database of historical crude oil data and fitting data from the database to determine a threshold level. As additional data on new crude oils or other feedstocks becomes available, the additional data can be incorporated into the database and used to modify the threshold levels. For clarity, isoparaffins are defined as non-cyclic alkanes and that include at least one side chain containing one or more carbon atoms.

Viscosity Index of Dewaxed Distillate Fractions

Although identifying crude fractions with a distillate portion having an isoparaffin content of 12 wt % or less can allow for exclusion of challenged crudes from use for lubricant base oil production, this type of identification will also lead to exclusion of some suitable crudes/feedstocks. In some aspects, suitable feedstocks for lubricant base oil production that have an isoparaffin content of 12 wt % or less can be identified by further characterizing the distillate portion of a feedstock. This further characterization can include determining the viscosity index (VI) value for the distillate portion after dewaxing the distillate portion to a target pour point, such as a target pour point of −9° C.

Determining a VI value for a dewaxed distillate portion at a pour point can be determined by any convenient method. One option is to measure the VI value for a dewaxed distillate fraction at the desired or target pour point. After forming the distillate portion, the distillate portion can be solvent dewaxed as described above. The severity of the solvent dewaxing can be sufficient for achieving a desired pour point, such as 0° C. or less, −6° C. or less, or −9° C. or less. The viscosity index of the dewaxed distillate fraction can then be directly measured, such as by measuring the viscosity of the dewaxed distillate at two different temperatures. Any convenient temperatures can be selected, such as 40° C., 100° C., 130° C., or other convenient temperatures.

Figure 3:
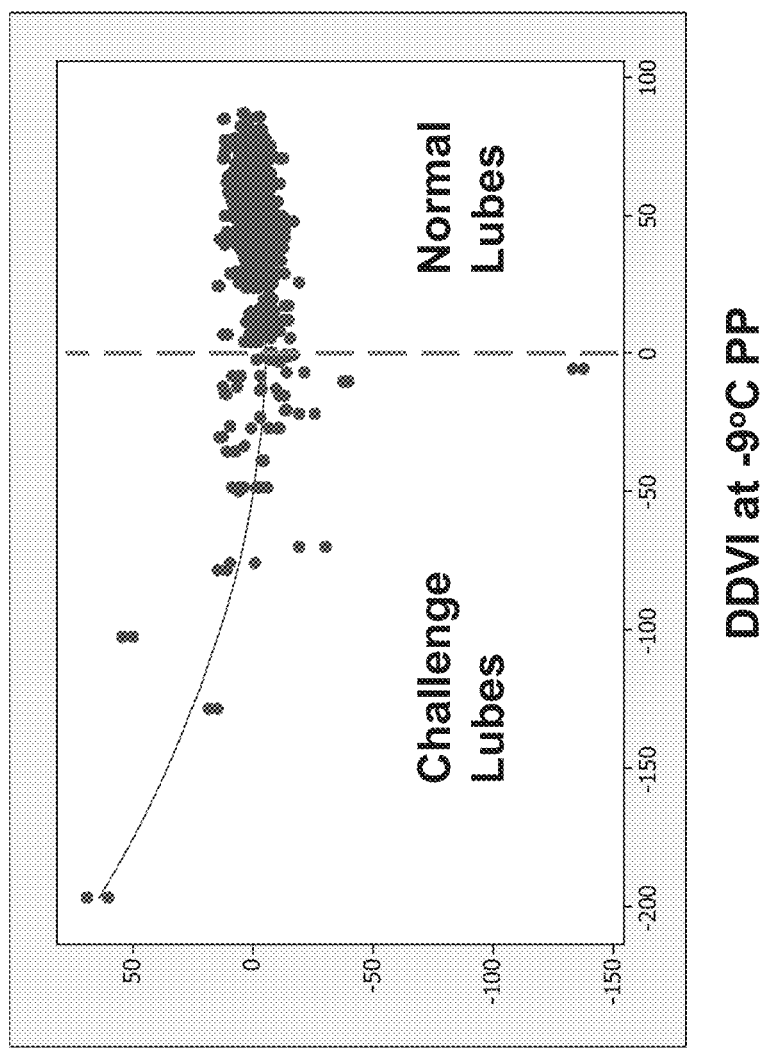
FIG. 3 shows dewaxed distillate viscosity index values for distillate fractions having a pour point of −9° C. for a variety of crude samples.

FIG. 3 shows an example of the distinction between a challenged crude and a suitable crude for lubricant base oil production based on the viscosity index value at a pour point of −9° C. (The vertical axis shows an additional indexing value for a crude to make it easier to view the number of samples that have a given viscosity index value.) In FIG. 3, the viscosity index values at a pour point of −9° C. are shown for the challenged and suitable crudes displayed in FIGS. 1 and 2. As shown in FIG. 3, all of the challenged crudes displayed in the plot have a viscosity index of less than zero at a pour point of −9° C. By contrast, all of the suitable crudes have a positive viscosity index. As a result, comparing the viscosity index of a crude oil at a given pour point with a threshold viscosity index value can allow for suitable crudes with low isoparaffin content to be identified and used for lubricant base oil production, while feedstocks with both low isoparaffin content and low VI at the given pour point can be excluded. It is noted that other pour points can be used as the given pour point value, but the dividing line between suitable and challenged crudes may correspond to a different VI value. The threshold value used for the viscosity index and/or the target pour point can also be updated in a manner similar to the method described above for updating the target isoparaffin, naphthene, and aromatics content threshold values.

Additional Embodiments

Embodiment 1. A method of evaluating a feedstock comprising: obtaining an isoparaffin content of a first distillate fraction from a first portion of a feedstock; determining that the isoparaffin content of the first distillate fraction is greater than a threshold level for isoparaffin content, the threshold level for isoparaffin content corresponding to an isoparaffin content of at least 12 wt %; determining that at least one of a naphthene content and an aromatics content of the first distillate fraction is within threshold levels; and solvent dewaxing at least a portion of a second distillate fraction from a second portion of the feedstock to form a lubricant base oil.

Embodiment 2. A method of evaluating a feedstock comprising: obtaining an isoparaffin content of a first distillate fraction from a first portion of a feedstock; determining that the isoparaffin content of the first distillate fraction is less than a threshold level for isoparaffin content, the threshold level for isoparaffin content corresponding to an isoparaffin content of at least 12 wt %; separating at least a portion of a second distillate fraction from a second portion of the feedstock to form a separated distillate fraction having a kinematic viscosity between 3.5 cSt and 16.5 cSt; solvent dewaxing at least a portion of the separated distillate fraction to a pour point target temperature to form a solvent dewaxed fraction; measuring the viscosity index of the solvent dewaxed fraction; determining that the viscosity index of the solvent dewaxed fraction is greater than a threshold viscosity index value; solvent dewaxing at least a portion of a third distillate fraction from a third portion of the feedstock to form a lubricant base oil.

Embodiment 3. The method of Embodiment 2, wherein separating at least a portion of a second distillate fraction from a second portion of the feedstock to form a separated distillate fraction having a kinematic viscosity between 3.5 cSt and 16.5 cSt comprises cutting the separated distillate fraction to a kinematic viscosity at 100° C. of between 3.8 to 4.2 cSt for a 100N visgrade base oil, a kinematic viscosity at 100° C. of between 5.1 to 5.8 cSt for a 150N visgrade base oil, or a kinematic viscosity at 100° C. of between 13.8 to 16.2 cSt for a 600N visgrade base oil.

Embodiment 4. The method of Embodiments 2 or 3, wherein the at least a portion of the separated distillate fraction is solvent dewaxed to a pour point target temperature of −9° C.

Embodiment 5. The method of any of Embodiments 2-4, wherein the threshold viscosity index value is 0.

Embodiment 6. The method of any of the above embodiments, further comprising: obtaining at least one of a naphthene content and an aromatics content of a distillate fraction from a portion of the feedstock; comparing the at least one of a naphthene content and an aromatics content to one or more threshold levels for naphthene content or aromatics content; and determining that the at least one of a naphthene content and an aromatics content satisfies the one or more threshold levels for naphthene content or aromatics content.

Embodiment 7. The method of Embodiment 6, wherein the threshold levels for isoparaffin content, naphthene content, and aromatics content are based on a database of crude oils for lube products.

Embodiment 8. The method of any of the above embodiments, wherein obtaining the isoparaffin content, the naphthene content, the aromatics content, or a combination thereof for a distillate fraction of a feedstock comprises: distilling a sample of the feedstock to obtain a sample distillate fraction; and measuring the isoparaffin content, naphthene content, aromatics content, or a combination thereof of the sample distillate fraction.

Embodiment 9. The method of Embodiment 8, wherein the isoparaffin content, the naphthene content, the aromatics content, or a combination thereof the sample distillate fraction is measured by NMR or gas chromatography.

Embodiment 10. The method of any of Embodiments 1-7, wherein obtaining the isoparaffin content, the naphthene content, the aromatics content, or a combination thereof for a distillate fraction of a feedstock comprises using high pressure liquid chromatography and gas chromatography time-of-flight mass spectrometry to determine directly the isoparaffin content, naphthene content, aromatics content, or a combination thereof for the distillate fraction without distilling the feedstock to separate out the distillate.

Embodiment 11. The method of any of the above embodiments, wherein a first threshold level for the naphthene content is at least 20 wt % and a second threshold level for the naphthene content is 80 wt % or less.

Embodiment 12. The method of any of the above embodiments, wherein a first threshold level for the aromatics content is at least 15 wt % and a second threshold level for the aromatics content is 80 wt % or less.

Embodiment 13. The method of any of the above embodiments, wherein the first distillate fraction, the second distillate fraction, the third distillate fraction, or a combination thereof have a boiling point range of 700° F. (371° C.) to 1100° F. (593° C.).

Embodiment 14. The method of any of the above embodiments, wherein the solvent dewaxing solvent is ketone, propane, or a combination thereof.

Embodiment 15. The method of any of the above embodiments, further comprising the steps of: evaluating a performance of a lubricant base oil formed from a second distillate fraction or a third distillate fraction based; incorporating the evaluated performance of the lubricant base oil along with at least one of an isoparaffin content, a naphthene content, an aromatics content, or viscosity index of a dewaxed distillate fraction for the second distillate fraction or the third distillate fraction into the database of crude oils; and modifying at least one of a threshold level or a target pour point.

Embodiment 16. The method of any of the above embodiments, wherein the feedstock is a crude oil, a crude oil fraction, a mixture of crude oils, or a combination thereof.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method of evaluating a feedstock comprising:
obtaining an isoparaffin content of a first distillate fraction from a first portion of a feedstock;
determining that the isoparaffin content of the first distillate fraction is greater than a threshold level for isoparaffin content, the threshold level for isoparaffin content corresponding to an isoparaffin content of at least 12 wt %;
determining that at least one of a naphthene content and an aromatics content of the first distillate fraction is within threshold levels; and
solvent dewaxing at least a portion of a second distillate fraction from a second portion of the feedstock to form a lubricant base oil.

2. The method of claim 1, wherein the threshold levels for isoparaffin content, naphthene content, and aromatics content are based on a database of crude oils for lube products.

3. The method of claim 1, wherein obtaining the iosparaffin content, the naphthene content, the aromatics content, or a combination thereof for a distillate fraction of a feedstock comprises:
distilling a sample of a crude oil to obtain a first distillate fraction; and
measuring the isoparaffin content, naphthene content, aromatics content, or a combination thereof of the first distillate fraction.

4. The method of claim 3, wherein the isoparaffin content, the naphthene content, the aromatics content, or a combination thereof of the first distillate fraction are measured by NMR or gas chromatography.

5. The method of claim 1, wherein obtaining the isoparaffin content, the naphthene content, the aromatics content, or a combination thereof for the first distillate fraction of a feedstock comprises using high pressure liquid chromatography and gas chromatography time-of-flight mass spectrometry to determine directly the isoparaffin content, naphthene content, aromatics content, or a combination thereof for the first distillate fraction without distilling the feedstock to separate out the distillate.

6. The method of claim 1, wherein a first threshold level for the naphthene content is at least 20 wt % and a second threshold level for the naphthene content is 80 wt % or less.

7. The method of claim 1, wherein a first threshold level for the aromatics content is at least 15 wt % and a second threshold level for the aromatics content is 80 wt % or less.

8. The method of claim 1, wherein the first distillate fraction, the second distillate fraction, or a combination thereof have a boiling point range of 700° F. (371° C.) to 1100° F. (593° C.).

9. The method of claim 1, wherein the feedstock is a crude oil, a crude oil fraction, a mixture of crude oils, or a combination thereof.

10. A method of evaluating a feedstock comprising:
obtaining an isoparaffin content of a first distillate fraction from a first portion of a feedstock;
determining that the isoparaffin content of the first distillate fraction is less than a threshold level for isoparaffin content, the threshold level for isoparaffin content corresponding to an isoparaffin content of at least 12 wt %;
separating at least a portion of a second distillate fraction from a second portion of the feedstock to form a separated distillate fraction having a kinematic viscosity between 3.5 cSt and 16.5 cSt;
solvent dewaxing at least a portion of the separated distillate fraction to a pour point target temperature to form a solvent dewaxed fraction;
measuring the viscosity index of the solvent dewaxed fraction;
determining that the viscosity index of the solvent dewaxed fraction is greater than a threshold viscosity index value;

solvent dewaxing at least a portion of a third distillate fraction from a third portion of the feedstock to form a lubricant base oil.

11. The method of claim 10, wherein separating at least a portion of a second distillate fraction from a second portion of the feedstock to form a separated distillate fraction having a kinematic viscosity between 3.5 cSt and 16.5 cSt comprises cutting the separated distillate fraction to a kinematic viscosity at 100° C. of between 3.8 to 4.2 cSt for a 100N visgrade base oil, a kinematic viscosity at 100° C. of between 5.1 to 5.8 cSt for a 150N visgrade base oil, or a kinematic viscosity at 100° C. of between 13.8 to 16.2 cSt for a 600N visgrade base oil.

12. The method of claim 10, wherein the at least a portion of the separated distillate fraction is solvent dewaxed to a pour point target temperature of −9° C.

13. The method of claim 10, wherein the threshold viscosity index value is 0.

14. The method of claim 10, wherein the first distillate fraction, the second distillate fraction, the third distillate fraction, or a combination thereof have a boiling point range of 700° F. (371° C.) to 1100° F. (593° C.).

15. The method of claim 10, wherein the solvent dewaxing solvent is ketone, propane, or a combination thereof.

16. The method of claim 10, further comprising the steps of:
    evaluating a performance of a lubricant base oil formed from a second distillate fraction or a third distillate fraction based;
    incorporating the evaluated performance of the lubricant base oil along with at least one of an isoparaffin content, a naphthene content, an aromatics content, or viscosity index of a dewaxed distillate fraction for the second distillate fraction or the third distillate fraction into the database of crude oils; and
    modifying at least one of a threshold level or a target pour point.

17. The method of claim 10, wherein the feedstock is a crude oil, a crude oil fraction, a mixture of crude oils, or a combination thereof.

* * * * *